United States Patent [19]

Revis

[11] Patent Number: 4,912,242

[45] Date of Patent: Mar. 27, 1990

[54] PROCESS FOR PREPARING SILICON ESTERS

[75] Inventor: Anthony Revis, Freeland, Mich.

[73] Assignee: Dow Corning Corporation, Midland, Mich.

[21] Appl. No.: 351,639

[22] Filed: May 15, 1989

[51] Int. Cl.$^4$ .............................. C07F 7/08; C07F 7/18
[52] U.S. Cl. ...................................................... 556/442
[58] Field of Search ......................................... 556/442

[56] References Cited

U.S. PATENT DOCUMENTS

| | | | |
|---|---|---|---|
| 4,332,956 | 6/1982 | Tolentino | 556/442 |
| 4,680,365 | 7/1987 | Müller et al. | 556/442 X |
| 4,746,750 | 5/1988 | Revis | 556/443 |

*Primary Examiner*—Paul F. Shaver
*Attorney, Agent, or Firm*—Jim L. DeCesare

[57] ABSTRACT

A process of preparing silicon esters involving contacting an allyl ester with a silicon hydride in the presence of a Group VIII metal catalyst. The molar ratio between the allyl ester and the silicon hydride is less than about 1:1, and the silicon ester is separated and isolated.

10 Claims, No Drawings

PROCESS FOR PREPARING SILICON ESTERS

BACKGROUND OF THE INVENTION

This invention relates to a method of preparing silicon esters. For purposes of the invention, the term silicon ester is intended to include acyloxy silanes and acyloxy siloxanes. More particularly, the invention is directed to a process in which an allyl ester is contacted with a silicon hydride, and in the presence of a Group VIII metal catalyst.

Acetoxy silanes and acyloxy silanes are useful materials as silylating ingredients, and as cross-linkers in the production of moisture cure silicone sealants. Known methods of preparing acetoxy and acyloxy silanes involve the reaction of chlorosilanes with acetic acid, acetic anhydride, organic carboxylic acids, organic anhydrides, and carboxylate salts. Other known methods require the reaction between carboxylic acids and silazanes; exchange reactions involving alkoxysilanes and organic anhydrides; and reactions of carboxylic acids and aminosilanes. Such processes, however, often result in the formation of complex mixtures which cannot be readily separated. Acyloxy silanes have been produced with carboxylic acids, hydridosilanes, and a transition metal catalyst, however, the generation of hydrogen gas has limited the use of this process commercially. In U.S. Pat. No. 4,746,750, issued May 24, 1988, a process is described for preparing silyl ketene acetals from allyl 2-organoacrylates and trisubstituted silanes. The process of the present invention is similar to the process described in the '750 patent. The basic difference, however, between the method of the present invention and the method of the '750 patent, is that the '750 patent requires a molar ratio between the 2-organoacrylate and the silane of greater than 1:1, typically 1:2. In accordance with the method of the present invention, however, there is required a ratio less than about 1:1. As a result, it is only possible in accordance with the method of the present invention, to prepare and isolate a silicon ester, and not a silyl ketene acetal as in the '750 patent.

SUMMARY OF THE INVENTION

This invention relates to a process of preparing silicon esters which include acyloxy silanes and acyloxy siloxanes involving contacting an allyl ester with a silicone hydride in the presence of a Group VIII metal catalyst, the molar ratio between the allyl ester and the silicon hydride being less than about 1:1, and separating and isolating the silicon ester.

The allyl ester employed in the process can be allyl butyrate, allyl acetate, allyl methacrylate, vinyl acetate, allyl acrylate, vinyl butyrate, and other known allyl esters. For purposes of the present invention, the term silicon hydride is intended to include any compound containing at least one hydrogen bonded to silicon. Accordingly, the silicon hydride employed herein can be a compound such as a silane or a siloxane. Typical silanes which may be employed in accordance with the present invention are bis(dimethylamino)methylsilane, bis(dimethylsilyl)benzene, bis(dimethylsilyl)phenylether, chloromethyldimethylsilane, dichlorosilane, diethylsilane, diethylmethylsilane, diethylaminomethylethoxysilane, dimethylchlorosilane, dimethylethoxysilane, dimethylsilane, diphenylchlorosilane, diphenylmethylsilane, diphenylsilane, ethyldichlorosilane, ethyldimethylsilane, ethylsilane, hexyldichlorosilane, n-hexylsilane, methyldichlorosilane, methylphenylsilane, methylsilane, octadecylsilane, octylsilane, phenyldichlorosilane, phenyldimethylsilane, phenylmethylchlorosilane, phenylmethylvinylsilane, phenylsilane, tetramethyldisilylethylene, trichlorosilane, triethoxysilane, triethylsilane, trihexysilane, triisopropylsilane, trimethoxysilane, trimethyldisilane, trimethylsilane, tri-n-octylsilane, triphenylsilane, and tri-n-propylsilane. Siloxanes which may be used are bis(trimethylsiloxy)dimethyldisiloxane, bis(trimethylsiloxy)methylsilane, diphenyldimethyldisiloxane, diphenyltetrakis(dimethylsiloxy)disiloxane, heptamethyltrisiloxane, hexamethyltrisiloxane, methylhydrocyclosiloxanes, methyltris(dimethylsiloxy)silane, octamethyltetrasiloxane, pentamethylcyclopentasiloxane, pentamethyldisiloxane, phenyltris(dimethylsiloxy)silane, polymethylhydrosiloxane, tetrakis(dimethylsiloxy)silane, tetramethylcyclotetrasiloxane, and tetramethyldisiloxane.

The preferred Group VIII metal catalyst is $RhCl_3$, although other appropriate catalyst systems may be employed such as $ClRh(PPh_3)_3$; $H_2PtCl_6$; a complex of 1,3-divinyl tetramethyl disiloxane and $H_2PtCl_6$; and alkyne complexes of $H_2PtCl_6$. A more exhaustive list of appropriate catalyst systems is set forth in the '750 patent, which is considered incorporated herein by reference. The most effective concentration of the Group VIII metal catalyst has been found to be from about ten parts per million to about two thousand parts per million on a molar basis relative to the allyl ester.

Exemplary of the silicon esters produced in accordance with the present invention are, for example, trimethylsilyl butyrate, trimethylsilyl methacrylate, t-butyldimethylsilyl methacrylate, trimethylsilyl acetate, phenyldimethylsilyl acetate, phenyldimethylsilyl butyrate, dimethylchlorosilyl butyrate, and phenyldimethylsilyl methacrylate. Other compounds such as tetramethyldisiloxy 1,3-dibutyrate can also be produced.

While many conventional techniques may be employed to separate and isolate the acyloxy silanes and acyloxy siloxanes produced by the process of the present invention, the recovery technique most preferred in accordance with the present invention for the isolation of the silicon ester is distillation.

These and other features, advantages, and objects, of the present invention will become more apparent when considered in light of the following detailed description thereof.

DETAILED DESCRIPTION OF THE INVENTION

The production of the silicon esters in accordance with the process of the present invention proceeds in accordance with the mechanism set forth in the following reaction:

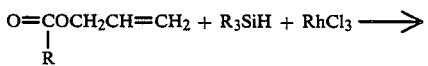

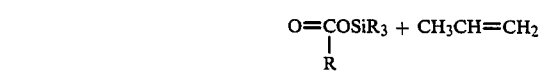

where R is alkyl, aryl, alkaryl, alkenyl, or substituted alkyl, aryl, alkaryl, and alkenyl groups.

As noted above, it is important to maintain a molar ratio between the allyl ester and the silicon hydride of less than about 1:1 in order to form and isolate the silicon ester in the form of an alcyloxy silane or as an acyloxy siloxane. Where R in the above equation is alkenyl, and when the molar ratio is in excess of about 1:1, typically 1:2 for example, there is formed and isolated a silyl ketene acetal of the type depicted in the '750 patent.

Following are several examples illustrating the process of the present invention including the production of various silicon esters with allyl esters and silicon hydrides. In the examples, GCMS refers to gas chromatography mass spectroscopy; GC is gas chromatography; and THF is tetrahydrofuran. Hydrosilylation was carried out in a two hundred-fifty milliliter three neck round bottom flask equipped with an addition funnel, a cold water condenser, a thermocouple, magnetic stirrer, and a controlled heating mantle, unless otherwise indicated. Volatile removal and isolation of the crude product was performed by rotary evaporation distillation instead of overhead distillation. Gas chromatography was utilized in order to determine the area percent purity of the acyloxy silane and acyloxy siloxane products. Toluene indicated as $PhCH_3$ in the several examples was added as an internal gas chromatography standard and otherwise had no effect on the reaction or the yield of the products produced by the method. Identification of the product was performed by gas chromatography mass spectroscopy and infrared spectroscopy.

EXAMPLE I

Reaction of Allyl Acetate with $Me_3SiH$ Catalyzed by $RhCl_3$

To a solution of 0.20 g (2.0 mmol) of allyl acetate, 0.6 g of 0.03M $RhCl_3$/THF, and 0.06 g of $PhCH_3$ in a 2 oz glass vial, was added 0.20 g (2.7 mmol) of $Me_3SiH$. The reaction mixture was stirred at room temperature for 24 hours and analyzed. GCMS data confirmed the formation of trimethylsilyl acetate. The GC calculated yield was 60%.

EXAMPLE II

Reaction of Allyl Acetate with $Me_3SiH$ Catalyzed by $H_2PtCl_6$

Example I was repeated with $H_2PtCl_6$. Trimethylsilyl acetate was formed but in a lesser amount.

EXAMPLE III

Reaction of Allyl Butyrate with $Me_3SiH$ Catalyzed by $RhCl_3$

To a solution of 2.56 g (20.0 mmol) of allyl butyrate, 0.6 g of 0.03M $RhCl_3$/THF, and 0.20 g of $PhCH_3$ in a 2 oz glass vial, was added 1.74 g (23.5 mmol) of $Me_3SiH$. The reaction mixture was stirred at room temperature with venting to release propene. The reaction was exothermic and turned light brown to dark brown in color within 10 min. GCMS showed a product identified as trimethylsilyl butyrate. The GC calculated yield was 65%.

EXAMPLE IV

Reaction of Allyl Butyrate with $Me_3SiH$ Catalyzed by $H_2PtCl_6$

Example III was repeated with $H_2PtCl_6$. There was formed a lesser amount of the product trimethylsilyl butyrate.

EXAMPLE V

Reaction of Allyl Acetate with $PhMe_2SiH$

A solution of 20 g (20.0 mmol) of allyl acetate, 2.15 ml (300 molar ppm) of 0.03M $RhCl_3$/THF solution, and 0.50 $PhCH_3$ was heated to 82° C. When several drops of silane were added, the temperature increased to 87° C. which indicated an exothermic reaction. The silane was added slowly over a temperature range of 87° C. to 115° C. The process of adding silane and external heating was repeated until the allyl acetate was consumed. A total of 30 g (0.22 mol) of silane was employed, and a crude weight of 45.51 g was removed. Phenyldimethylsilyl acetate was identified by GCMS as the major component of the mixture. The isolated sample was compared with an independently synthesized sample and the GCMS spectra matched. A total of 11.52 g of material was isolated which indicated 89% by GC area of phenyldimethylsilyl acetate.

EXAMPLE VI

Reaction of Allyl Butyrate with $PhMe_2SiH$

A solution of 25.6 g (0.20 mol) of allyl butyrate, 2.15 mo (300 molar ppm) of 0.03M $RhCl_3$/THF solution, and 1.20 g of $PhCH_3$, was heated to 80° C. When 2 ml of silane was added, the temperature increased to 93° C. The silane was added slowly with temperatures ranging from 80° C. to 95° C. The process of adding silane and external heating was repeated until the allyl butyrate ceased to react. A total of 30 g (0.22 mol) of silane was employed, and a crude weight of 50.79 g was removed from the flask. One major peak was formed and a sample was isolated and identified as phenyldimethylsilyl butyrate. The GCMS of the isolated sample was compared to that of known phenyldimethylsilyl butyrate and the GCMS spectra matched. A total of 44.82 g of material was isolated which indicated 79% by GC area of phenyldimethylsilyl butyrate.

EXAMPLE VII

Reaction of Allyl Butyrate with $ClMe_2SiH$

A solution of 15 g (0.12 mol) of allyl butyrate, 1.28 ml (300 molar ppm) of 0.03M $RhCl_3$/THF solution, and 1.50 g $PhCH_3$ was heated to 80° C. When 2 ml of silane was added, no reaction occurred. The temperature was increased to 96° C. and more drops of silane was added, but no reaction occurred. The temperature was raised to 103° C. and an exothermic reaction occurred. The process of adding silane and external heating was repeated until all of the silane (12.22 g, 0.13 mol) had been added at between 80° C. and 112° C. This provided a crude weight of 25.36 g. The crude product was stripped of volatiles leaving 7.67 g of 73% pure dimethylchlorosilyl butyrate based on GC area percent and GCMS.

EXAMPLE VIII

Reaction of Allyl Butyrate with Sym-Tetramethyldisiloxane

A solution of 15 g (0.12 mol) of allyl butyrate, 1.28 ml (300 molar ppm) of 0.03M $RhCl_3$/THF solution, and 1.52 g of $PhCH_3$ was heated to 85° C. When 2 ml of siloxane was added, the temperature increased to 95° C. and an exothermic reaction occurred. The siloxane was added slowly with temperatures ranging from 92° C. to 107° C. The process of adding siloxane and external heating was repeated until all siloxane was added. A total of 12.06 g (0.09 mol) of siloxane was employed providing a cure weight of 19.52 g. After rotary evaporation, 23.43 g was obtained and GC showed 89% of tetramethyldisiloxy 1,3-dibutyrate. GCMS matched an independently synthesized sample.

EXAMPLE IX

Reaction of Allyl Methacrylate with $PhMe_2SiH$

A solution of 50.46 g (0.40 mol) of allyl methacrylate, 1.00 g of 2,6-di-t-butyl-4-methylphenol (BHT) as a polymerization inhibitor, 4.28 ml of (300 molar ppm) 0.03 $RhCl_3$/THF solution, and 5.00 g of $PhCH_3$, was heated to 60° C. under a 2% $O_2$/98% $N_2$ purge. When several drops of silane was added, an exothermic reaction occurred, and the temperature increased to 80° C. When half of the silane was added, the exothermic reaction ceased, and the temperature decreased to 35° C. The heating mantel was employed to heat the reaction mixture to 101° C. An exothermic reaction occurred without additional silane. The process of adding silane and heating was repeated until 60.00 g (0.44 mol) of silane was added. The crude product weight was 114.11 g which contained phenyldimethylsilyl methacrylate as the major product based on GCMS. The GCMS of phenyldimethylsilyl methacrylate matched that of an independent sample. After removal of the volatiles, 30.16 g of crude mixture remained which contained 62% by GC area of phenyldimethylsilyl methacrylate.

EXAMPLE X $RhCl_3$ Catalyzed Reaction of Vinyl Acetate with $PhMe_2SiH$

A solution of 43.00 g (0.50 mol) of vinyl acetate, 5.36 ml (300 molar ppm) of 0.03M $RhCl_3$/THF solution, and 4.30 g of $PhCH_3$, were heated to 50° C. When 5 ml of silane was added, the temperature increased to 72° C. The silane was added slowly with temperatures ranging from 77° C. to 127° C. The process of adding silane and external heating was repeated until all silane was added (74.80 g, 0.55 mol) providing a crude weight of 121.13 g. After removal of volatiles by rotary evaporation, 93.73 g of crude mixture remained which contained 5% of phenyldimethylsilyl acetate.

EXAMPLE XI

Platinum Catalyzed Reaction of Vinyl Acetate with $PhMe_2SiH$

A solution of 43 g (0.50 mol) of vinyl acetate, 0.22 g of platinum concentrate, and 4.30 g of $PhCH_3$ was heated to 50° C. When 5 ml of silane was added, the temperature increased to 52° C. More silane was added drop-wise, but the temperature decreased and the reaction ceased. 0.10 g of platinum catalyst was added to the reaction mixture. The temperature increased to 60° C. indicating an exothermic reaction. The silane was added slowly with temperatures ranging from 60° C. to 92° C. The process of adding silane and external heating was repeated until all silane (74.80 g) was added providing a crude weight of 115.21 g. The sample was isolated by rotary evaporation and phenyldimethylsilyl acetate was identified by GCMS. After removal of the volatiles, 11.5 g of crude mixture remained which contained 5% of phenyldimethylsilyl acetate. The platinum catalyst concentrate used in this example was a complex of 1,3-divinyl tetramethyl disiloxane and $H_2PtCl_6$.

In some cases, there may be required a polymerization inhibitor such as 2,6-di-t-butyl-4-methylphenol(BHT) in Example IX, in order to minimize the polymerization of the alkenyl functionality. There may also be employed inhibitors such as hydroquinone, 4-methoxyphenol, and 4-methylphenol.

The reaction time employed in the processes in accordance with the present invention must at least exceed the time required in order to consume the allyl ester. As to the amounts of reactants, it has been found that an excess of at least about ten percent of the silicon hydride can be tolerated, except in those instances where the product will undergo further hydrosilylation. The catalyst concentration may vary from as low as twenty-five parts per million of rhodium to about two thousand parts per million, and for platinum 10–2000 ppm is preferred, although both types may be employed in concentrations generally within the range of 10–2000 ppm on a molar basis relative to the allyl ester.

It will be apparent from the foregoing that many other variations and modifications may be made in the structures, compounds, compositions, and methods described herein without departing substantially from the essential features and concepts of the present invention. Accordingly, it should be clearly understood that the forms of the invention described herein are exemplary only and are not intended as limitations on the scope of the present invention.

That which is claimed is:

1. A process of preparing a silicon ester comprising contacting an allyl ester with a silicon hydride in the presence of a Group VIII metal catalyst, the molar ratio between the allyl ester and the silicon hydride being less than about 1:1, and separating and isolating the silicon ester.

2. The process according to claim 1 wherein the allyl ester is selected from the group consisting of allyl butyrate, allyl acetate, allyl methacrylate, vinyl acetate, allyl acrylate, and vinyl butyrate.

3. The process according to claim 2 wherein the silicon hydride is selected from the group consisting of bis(dimethylamino)methylsilane, bis(dimethylsilyl)benzene, bis(dimethylsilyl)phenylether, chloromethyldimethylsilane, dichlorosilane, diethylsilane, diethylmethylsilane, diethylaminomethylethoxysilane, dimethylchlorosilane, dimethylethoxysilane, dimethylsilane, diphenylchlorosilane, diphenylmethylsilane, diphenylsilane, ethyldichlorosilane, ethyldimethylsilane, ethylsilane, hexyldichlorosilane, n-hexylsilane, methyldichlorosilane, methylphenylsilane, methylsilane, octadecylsilane, octylsilane, phenyldichlorosilane, phenyldimethylsilane, phenylmethylchlorosilane, phenylmethylvinylsilane, phenylsilane, tetramethyldisilylethylene, trichlorosilane, triethoxysilane, triethylsilane, trihexysilane, triisopropylsilane, trimethoxysilane, trimethyldisilane, trimethylsilane, tri-n-octylsilane, triphenylsilane, and tri-n-propylsilane.

4. The process according to claim 2 wherein the silicon hydride is selected fromthe group consisting of bis(trimethylsiloxy)dimethyldisiloxane, bis(trimethylsiloxy)methylsilane, diphenyldimethyldisiloxane, diphenyltetrakis(dimethylsiloxy)disiloxane, heptamethyltrisiloxane, hexamethyltrisiloxane, methylhydrocyclosiloxanes, methyltris(dimethylsiloxy)silane, octamethyltetrasiloxane, pentamethylcyclopentasiloxane, pentamethyldisiloxane, phenyltris(dimethylsiloxy)silane, polymethylhydrosiloxane, tetrakis(dimethylsiloxy)silane, tetramethylcyclotetrasiloxane, and tetramethyldisiloxane.

5. The process according to claim 2 wherein the Group VIII metal catalyst is RhCl$_3$.

6. The process according to claim 2 wherein the Group VIII metal catalyst is selected from the group consisting of ClRh(PPh$_3$)$_3$, H$_2$PtCl$_6$, a complex of 1,3-divinyl tetramethyl disiloxane and H$_2$PtCl$_6$, and alkyne complexes of H$_2$PtCl$_6$.

7. The process according to claim 2 wherein the concentration of the Group VIII metal catalyst is from about ten parts per million to about two thousand parts per million on a molar basis relative to the allyl ester.

8. The process according to claim 7 wherein the silicon ester is isolated by distillation.

9. The process according to claim 2 wherein the silicon ester is selected from the group consisting of trimethylsilyl butyrate, trimethylsilyl acetate, phenyldimethylsilyl acetate, phenyldimethylsilyl butyrate, dimethylchlorosilyl butyrate, phenyldimethylsilyl methacrylate, trimethylsilyl methacrylate, and t-butyldimethylsilyl methacrylate.

10. The process according to claim 2 wherein the silicon ester is tetramethyldisiloxy 1,3-dibutyrate.

* * * * *